US012708424B2

(12) United States Patent
Sommer

(10) Patent No.: US 12,708,424 B2
(45) Date of Patent: Aug. 18, 2026

(54) TRANSCATHETER CLOSURE OF PATENT FORAMEN OVALE WITH BIPOLAR RF APPLICATION

(71) Applicant: THE TRUSTEES OF COLUMBIA UNIVERSITY IN THE CITY OF NEW YORK, New York, NY (US)

(72) Inventor: Robert Jay Sommer, New Rochelle, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1017 days.

(21) Appl. No.: 17/499,361

(22) Filed: Oct. 12, 2021

(65) Prior Publication Data

US 2022/0022935 A1 Jan. 27, 2022

Related U.S. Application Data

(63) Continuation of application No. PCT/US2020/027974, filed on Apr. 13, 2020.

(60) Provisional application No. 62/833,000, filed on Apr. 12, 2019.

(51) Int. Cl.

| | |
|---|---|
| ***A61B 18/12*** | (2006.01) |
| ***A61B 18/14*** | (2006.01) |
| *A61B 18/00* | (2006.01) |

(52) U.S. Cl.

CPC .......... *A61B 18/1206* (2013.01); *A61B 18/14* (2013.01); *A61B 2018/00077* (2013.01); *A61B 2018/0038* (2013.01); *A61B 2018/126* (2013.01); *A61B 2018/1405* (2013.01)

(58) Field of Classification Search

CPC ................ A61B 18/1206; A61B 18/14; A61B 2018/00077; A61B 2018/0038; A61B 2018/126; A61B 2018/1405; A61B 18/1492; A61B 2018/0063; A61B 2018/1475

See application file for complete search history.

(56) References Cited

U.S. PATENT DOCUMENTS

| | | | |
|---|---|---|---|
| 6,939,348 | B2 | 9/2005 | Malecki |
| 7,186,251 | B2 | 3/2007 | Malecki et al. |
| 7,257,450 | B2 | 8/2007 | Auth et al. |
| 7,473,252 | B2 | 1/2009 | Barry |
| 7,797,056 | B2 | 9/2010 | Forde et al. |
| 7,972,330 | B2 | 7/2011 | Alejandro et al. |
| 8,021,359 | B2 | 9/2011 | Auth |
| 8,038,669 | B2 | 10/2011 | Malecki et al. |
| 8,038,672 | B2 | 10/2011 | Malecki et al. |
| 8,052,678 | B2 | 11/2011 | Malecki et al. |
| 8,075,554 | B2 | 12/2011 | Malecki et al. |
| 8,095,212 | B2 | 1/2012 | Sato |
| 8,109,274 | B2 | 2/2012 | Horne et al. |

(Continued)

OTHER PUBLICATIONS

International Search Report and Written Opinion cited in PCT/US20/27974 dated Jul. 1, 2020, 10 pages.

*Primary Examiner* — Joanne M Rodden
*Assistant Examiner* — Dana Stumpfoll
(74) *Attorney, Agent, or Firm* — BakerHostetler

(57) ABSTRACT

Apparatus and method for closure of the patent foramen ovale (PFO) is provided using expandable discs to appose the septum primum and septum secundum and to apply bipolar radiofrequency energy to anneal the tissues.

20 Claims, 16 Drawing Sheets

(56) References Cited

U.S. PATENT DOCUMENTS

| | | | | |
|---|---|---|---|---|
| 8,221,405 | B2 * | 7/2012 | Whisenant | A61B 5/053 606/41 |
| 8,308,723 | B2 | 11/2012 | Kulesa et al. | |
| 2005/0119647 | A1 * | 6/2005 | He | A61B 18/1492 606/41 |
| 2007/0203479 | A1 * | 8/2007 | Auth | A61B 18/1492 606/41 |
| 2007/0287999 | A1 | 12/2007 | Malecki et al. | |
| 2008/0033421 | A1 * | 2/2008 | Davis | A61B 17/0057 606/41 |
| 2008/0300590 | A1 | 12/2008 | Horne et al. | |
| 2009/0131925 | A1 * | 5/2009 | Tempel | A61B 18/1492 606/213 |
| 2010/0087811 | A1 | 4/2010 | Herrin et al. | |
| 2011/0218503 | A1 | 9/2011 | Kaveckis et al. | |
| 2011/0282345 | A1 | 11/2011 | Chanduszko et al. | |

* cited by examiner

TRANSCATHETER CLOSURE OF PATENT FORAMEN OVALE WITH BIPOLAR RF APPLICATION

CROSS-REFERENCE TO RELATED APPLICATIONS

This application is a continuation of International Application PCT/US2020/027974 filed Apr. 13, 2020, which claims benefit of priority to U.S. Provisional Application No. 62/833,000 filed Apr. 12, 2019, both of which are incorporated by reference in their entirety herein.

FIELD

Apparatus and method for closure of the patent foramen ovale (PFO) using bipolar radiofrequency energy application.

BACKGROUND

The foramen ovale is a normal flap in the heart wall (the septum) between the left and right atria of every human fetus, which allows blood to cross from the right side of the heart to the left. For about 75 percent of the population, the foramen ovale seals completely within a few months of birth. When it remains open, it is called a patent foramen ovale (PFO), and leaves a persistent pathway for blood to flow from right to left.

The presence of a PFO is associated with stroke or transient ischemic attack (TIA). Blood clots (thrombus) are a normal product in the veins of the body, and if dislodged can travel through the venous system to enter the right atrium of the heart. From there they are normally pumped into the right ventricle and then to the lungs, to be filtered by the tiny capillaries in the lungs. Post-filtration, the freshly oxygenated blood returns from the lungs to the left atrium, and then to the left ventricle. The left ventricle pumps the clean blood out into the arteries to supply oxygen to the body. The PFO provides a portal, or pathway through which a thrombus might be able to bypass the filtering mechanisms of the lungs, to cross directly from the right atrium to the left atrium, and then to travel to the brain, potentially causing stroke or TIA.

Transcatheter closure of the PFO is now a common procedure for patients who have suffered stroke, and is also currently linked mechanistically to migraine headaches. Currently approved technology, such as the GORE® CARDIOFORM Septal Occluder and the AMPLATZER™ PFO Occluder, involve closure of the PFO with an implantable "double umbrella" device. The devices are comprised of two expandable mesh-covered discs that sit on each side of the atrial septum and cover the defect. Over several months, the device is encapsulated/covered by the endothelium of the atrium by tissue ingrowth on the mesh material. Thereafter the device remains permanently in the septum.

Complications of current PFO closure devices include, e.g., a post-implant atrial fibrillation rate of about 5%; transient device wire frame fracture in the Cardioform Device of <10%; device thrombosis of <0.02%; and device erosion for the Amplatzer Device of <1%.

Even where implantation of the closure device is successful, the presence of a mechanical apparatus in the septum can present technical issues for subsequent procedures. For example, developments in interventional cardiac technologies have made possible repairs of rhythm disturbances (Radiofrequency ablation), elimination of stroke risk in patients with atrial fibrillation (left atrial appendage closure), and repair or even replacement of the mitral valve, all of which require passage of a large bore catheter from the right atrium to the left atrium through the atrial septum. The presence of the permanently implanted PFO closure device could interfere with the interventional procedure.

What is needed is an apparatus and method for sealing the PFO which avoids the disadvantages of current techniques, and eliminates the need for an implanted device altogether.

SUMMARY

In one aspect of the disclosure, a system for closure of the patent foramen ovale (PFO) is provided, including a tubular loader defining a lumen, a first RF applicator and a second applicator. The first RF applicator includes a first cable defining a distal end and a proximal end, a first disc coupled to the distal end of the first cable and insertable into the left atrium, the first disc fabricated from an electrically conductive, resilient material and defining an expanded disc-shaped configuration and a collapsed configuration for positioning within the lumen of the tubular loader; and a first contact at the proximal end of the first cable for electrical attachment to a bipolar RF generator. The second RF applicator includes a second cable defining a distal end and a proximal end, a second disc coupled to the distal end of the second cable and insertable into the right atrium, the second disc fabricated from an electrically conductive, resilient material and defining an expanded disc-shaped configuration and a collapsed configuration for positioning within the lumen of the tubular loader; and a second contact at the proximal end of the second cable for electrical attachment to the bipolar RF generator.

In some embodiments, the first and second discs are configured to expand to the expanded disc-shaped configuration upon deployment from the lumen of the tubular loader. In some embodiments, the system includes a tubular withdrawal member defining a lumen and insertable over the first cable and the first disc to collapse the first disc into the lumen of the tubular withdrawal member for withdrawal from the left atrium across the septum.

In some embodiments, the diameter of the first and second discs is about 1.5 cm to about 3.5 cm. In some embodiments, the second disc defines an aperture for the first cable to extend therethrough. In some embodiments, wherein the first and second discs are fabricated from a shape memory alloy. e.g., nitinol. In some embodiments, the length of the first and second cables is about 80 cm. In some embodiments, the system further includes a transseptal sheath.

In another aspect, a method of closure of the patent foramen ovale (PFO) is provided including inserting a distal end of a tubular loader into the left atrium of a subject's heart via the right atrium and the septum, deploying a first RF applicator within the tubular loader across the septum and into the left atrium, the first RF applicator comprising a first cable and a first disc fabricated from an electrically conductive, resilient material in a collapsed configuration within the tubular loader, deploying the first disc beyond the distal end of the tubular loading such that the first disc is allowed to resiliently expand from the collapsed configuration to an expandable disc-shaped configuration, withdrawing the first RF applicator such that the first disc is in apposition against the septum, withdrawing the tubular loader such that the distal end of the tubular loader is within the right atrium, deploying a second RF applicator within the tubular loader beyond the distal end of the tubular loader and into the right atrium, the second RF applicator comprising a second cable and a second disc fabricated from an electrically conductive, resilient material such that the second disc is allowed to resiliently expand from a collapsed position into an expanded disc-shaped configuration; advancing the second RF applicator such that the second disc is in apposition against the septum, thereby approximating the septum primum and septum secondum; and applying bipolar RF energy across the first and second disc to the septum via the first and second cables.

In some embodiments, inserting the distal end of the tubular loader into the left atrium of a subject's heart via the right atrium and the septum includes inserting the tubular loader through the PFO. In some embodiments, inserting the distal end of the tubular loader into the left atrium of a subject's heart via the right atrium and the septum includes inserting the tubular loader through a transseptal puncture.

In some embodiments, after applying bipolar RF energy across the first and second disc to the septum, the method includes withdrawing the second disc into the lumen of tubular loader. In some embodiments, the method includes providing a tubular withdrawal member. In some embodiments, the method includes advancing the tubular withdrawal member over the second cable into the right atrium. In some embodiments, the method includes withdrawing the second disc into the lumen of tubular withdrawal member. In some embodiments, the method includes withdrawing the tubular withdrawal member and the second RF applicator from the subject's heart.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF THE DISCLOSED SUBJECT MATTER

Reference will now be made in detail to select embodiments of the disclosed subject matter, examples of which are illustrated in the accompanying drawings. The method and corresponding steps of the disclosed subject matter will be described in conjunction with the detailed description of the system.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

As used herein and in the appended claims, the singular forms "a," "an," and "the" include plural referents unless the context clearly dictates otherwise.

In accordance with the various embodiments of the disclosed subject matter, as summarized above and as described in further detail below, there is provided systems, apparatuses and methods of transcatheter closure of PFO.

System Description

Figures 1, 2:
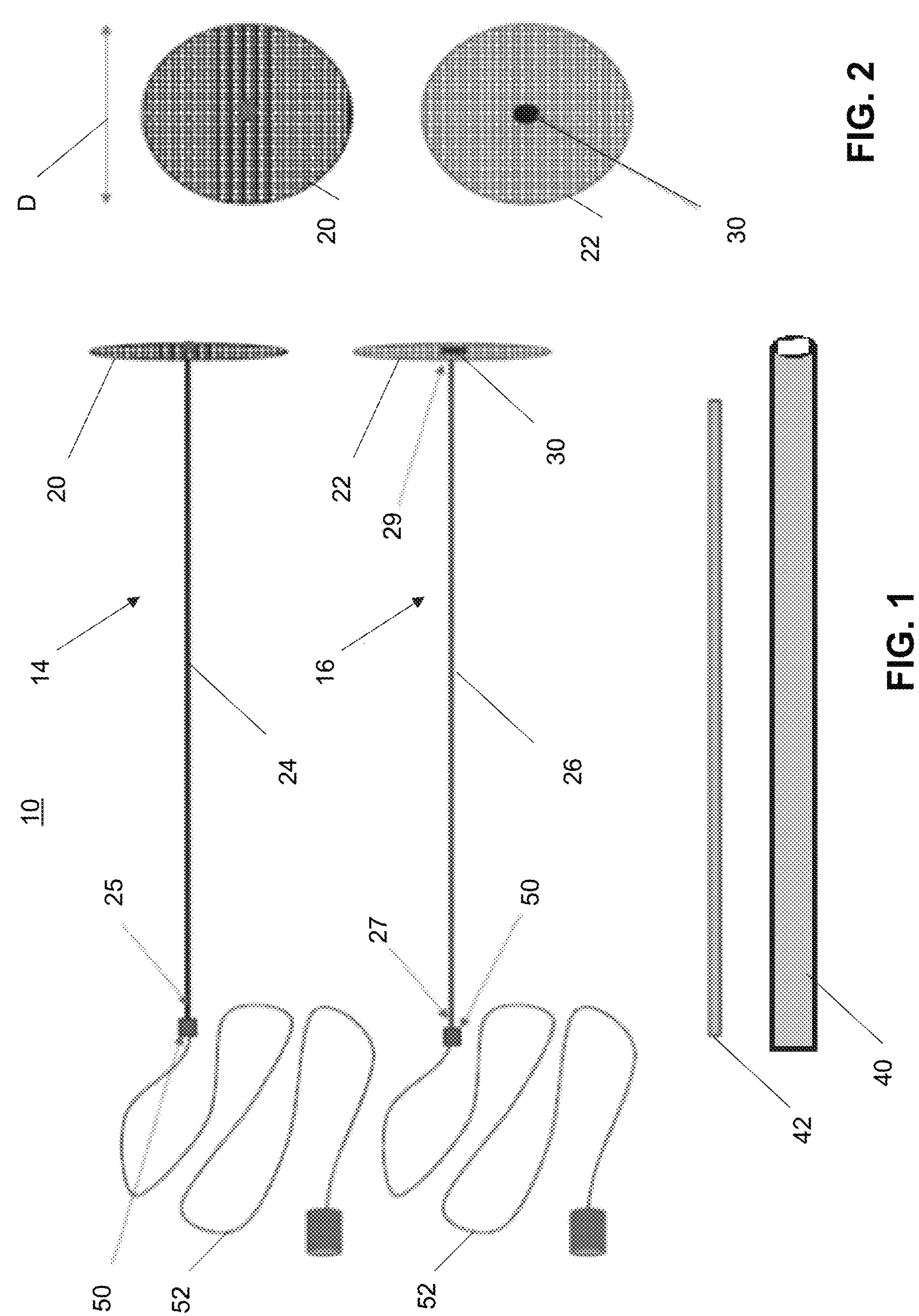
FIG. 1 is a schematic side view of the system in accordance with an exemplary embodiment of the disclosed subject matter.
FIG. 2 is an end view of the discs in accordance with an exemplary embodiment of the disclosed subject matter.

As illustrated in FIGS. 1-2, a system 10 in accordance with an exemplary embodiment is described herein. System 10 includes a transseptal sheath 12 (illustrated in FIGS. 3-4), e.g., 8-10 French, and a 0.032-0.035" J-wire which fits through its dilator.

A pair of RF applicators or "fryers" (e.g., left atrial "LA" RF applicator 14 and right atrial "RA" RF applicator 16), each made up of an expandable disc 20/22 of single thickness and having an electrically-isolated, permanently attached delivery wire or cable 24/26 of approximately 80 cm length. Discs 20/22 are fabricated from a shape memory alloy such as nitinol. It is understood that the size of the discs 20/22 will depend upon the size and characteristics of the defect to be treated. For example, discs can have a range of diameters D from 1.5 cm to 3.5 cm, e.g., 1.5 cm, 2 cm, 2.5 cm, 3 cm or 3.5 cm. (FIG. 2) The discs 20/22 are designed to be compressed or folded into a narrow tube (as described below) into a compressed configuration and to expand back to a disc shape upon being advanced or removed from the tube (the expanded configuration).

The LA RF applicator 14 includes a complete disc 20 and central cable 24. In order to align coaxially with the LA RF applicator 14, the RA RF applicator 16 has a central lumen 30. The distal portion 29 of cable 26 is slightly offset from lumen 30. The cable 24 of the LA RF applicator 14 can thread through lumen 30, as will be described below. Detachable RF conductor cables 52 connect the back of the delivery cables 24/26 of each RF applicator to the RF source, e.g., by PM connectors 50. In some embodiments, the proximal end portions 25/27 of the attached cables/wires 24/26, e.g., about 15 mm of cable, will be free of insulation to allow for the required electrical connection.

A tubular loading device 40 for the RF applicators 12/14, with attachment mechanism at the front end to allow closed seal introduction into the transseptal sheath 12 is provided. The outer dimension of the loader 40 is sized to fit within transseptal sheath 12. A co-pilot type adaptor for the back of the transseptal sheath to allow the cables to be fixed in position (not shown). A thin, rigid tubule 42 is provided which fits over the LA RF applicator cable 24 and through the transseptal sheath 12, long enough to reach the LA and collapse the disc 20 of the LA RF applicator 14, as will be described below.

Implantation of the device includes the following additional equipment: an RF generator; echo imaging equipment; and standard catheter and wires to cross the PFO, as are well-known in the art.

Method of Implantation

In some embodiments, the patient is loaded with antithrombotic agents to minimize risk of clot formation during the procedure. Such agents can include, e.g., dual antiplatelet therapy and heparin (ACT>250) during the procedure. Oral anticoagulation agents can be considered in special circumstances. Femoral venous access is obtained as is known in the art (e.g., one access, typically in the right femoral vein, if echo guidance is being performed with transesophageal echo (TEE), two accesses, typically at the right femoral vein, if intracardiac echo (ICE) is used. Anesthesia administration, for patient comfort, will depend in part on the type of echo imaging selected for the individual patient. When ICE is used, local anesthesia is used at the groin and intravenous conscious sedation is provided as needed. When TEE is used, most often, general endotracheal anesthesia is employed because of the discomfort associated with the TEE probe placement and manipulation.

Figure 3:
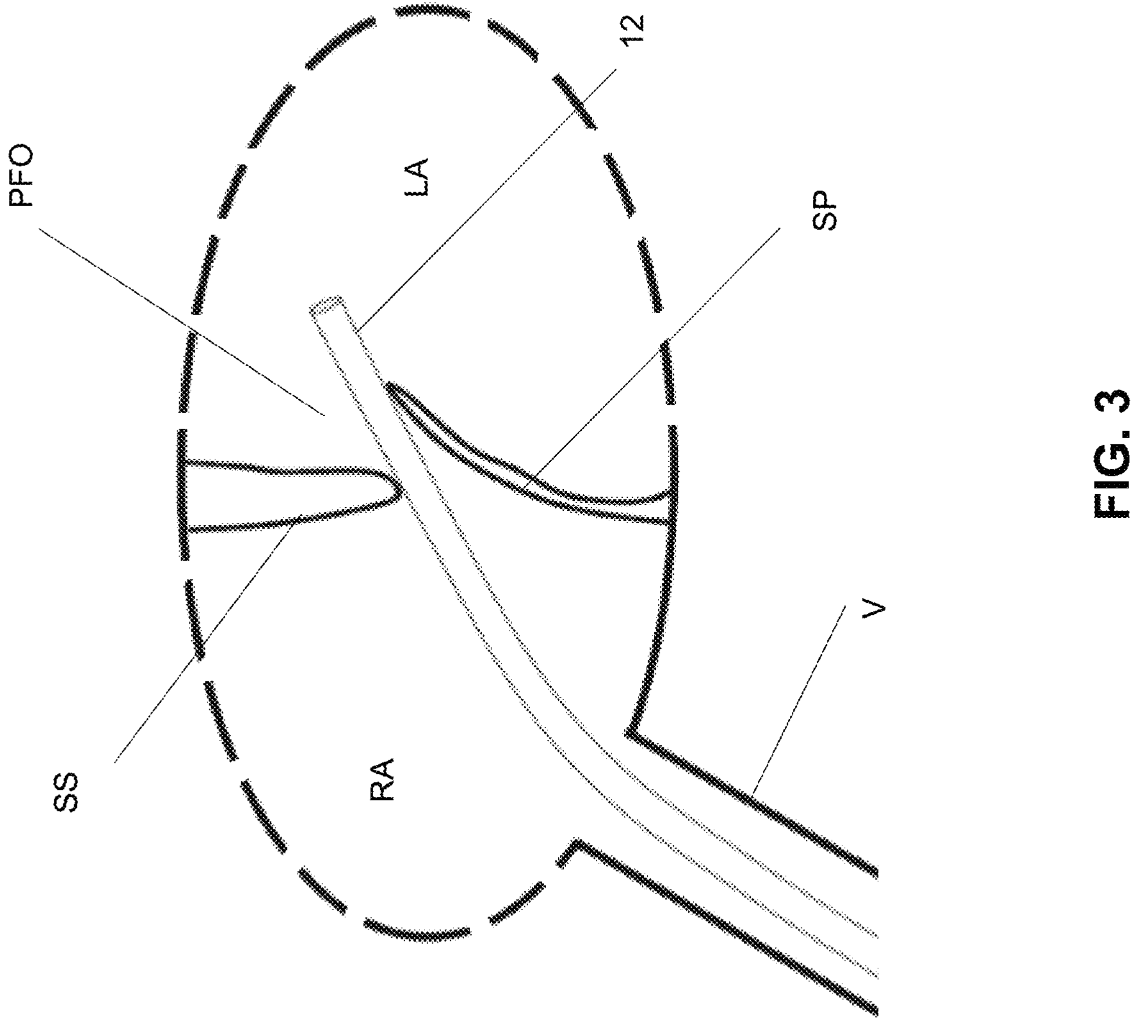
FIG. 3 is a schematic view in cross section of an early stage in the procedure in accordance with an exemplary embodiment of the disclosed subject matter.
Figure 4:
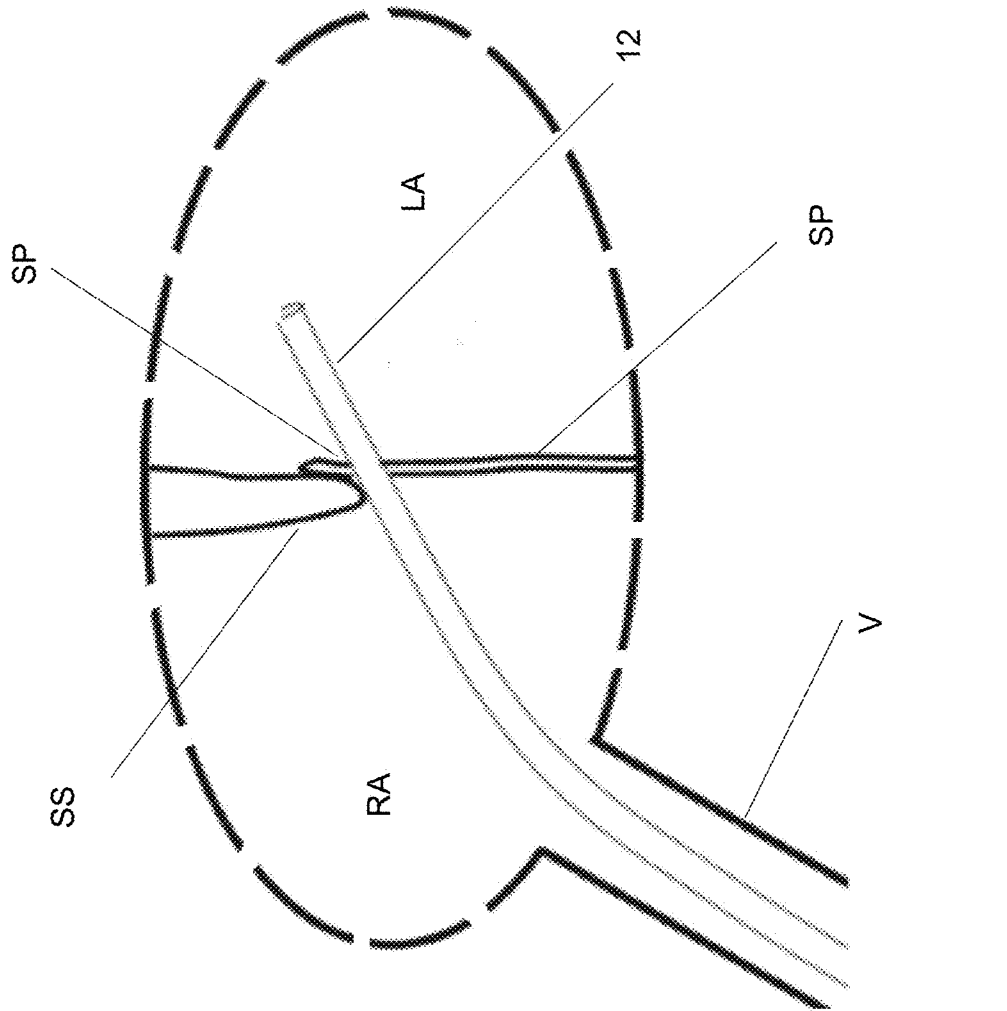
FIG. 4 is a schematic view in cross section of an early stage in the procedure in accordance with another exemplary embodiment of the disclosed subject matter.

Using well established techniques, with which all interventional congenital/structural physicians are typically familiar, a guidewire is passed through a vein V in the leg, through the right atrium RA, through the septum to the left atrium LA and is positioned in the left upper pulmonary vein. In some embodiments, the transseptal sheath 12 crosses the PFO directly (with a wire/catheter approach) as illustrated in FIG. 3. In some embodiments, a transseptal puncture SP is made through the septum primum SP, as close as possible to the site of overlap with the septum secundum, SS as illustrated in FIG. 4. The transseptal sheath 12 is advanced over the wire into the LA and the sheath dilator and guidewire are removed.

Figure 5:
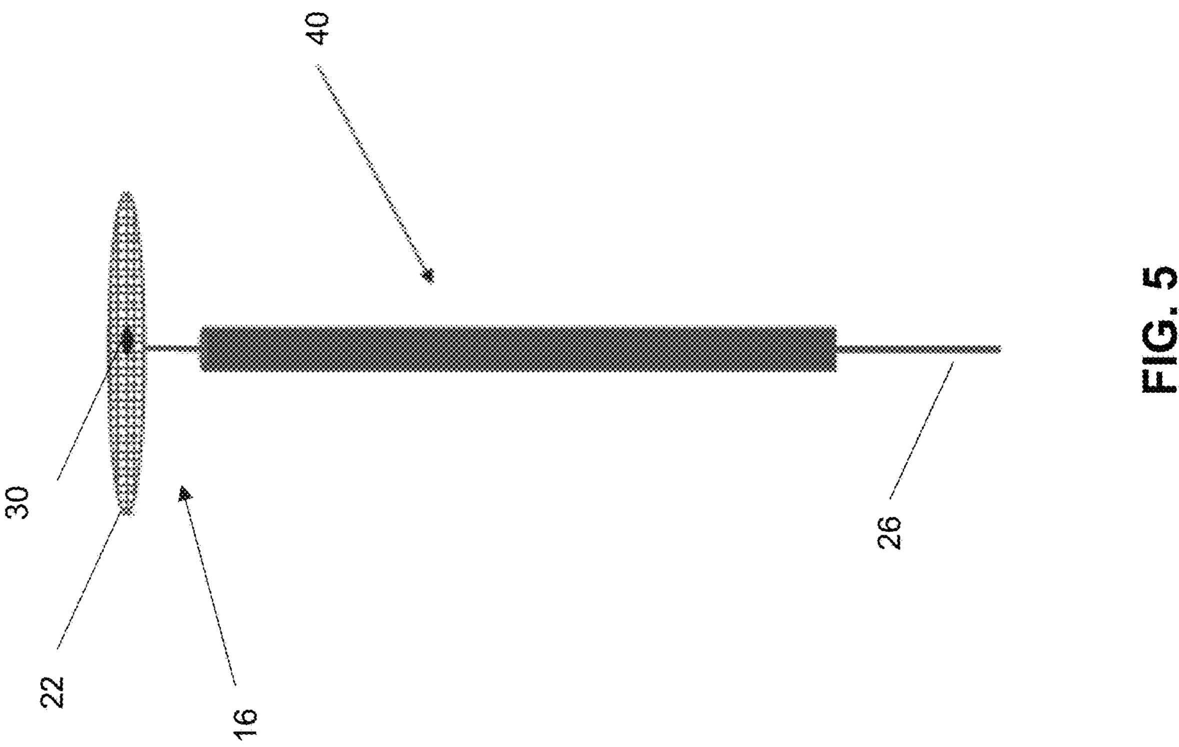
FIGS. 5-9 illustrate several stages of loading components of the system in accordance with an exemplary embodiment of the disclosed subject matter.
Figure 6:
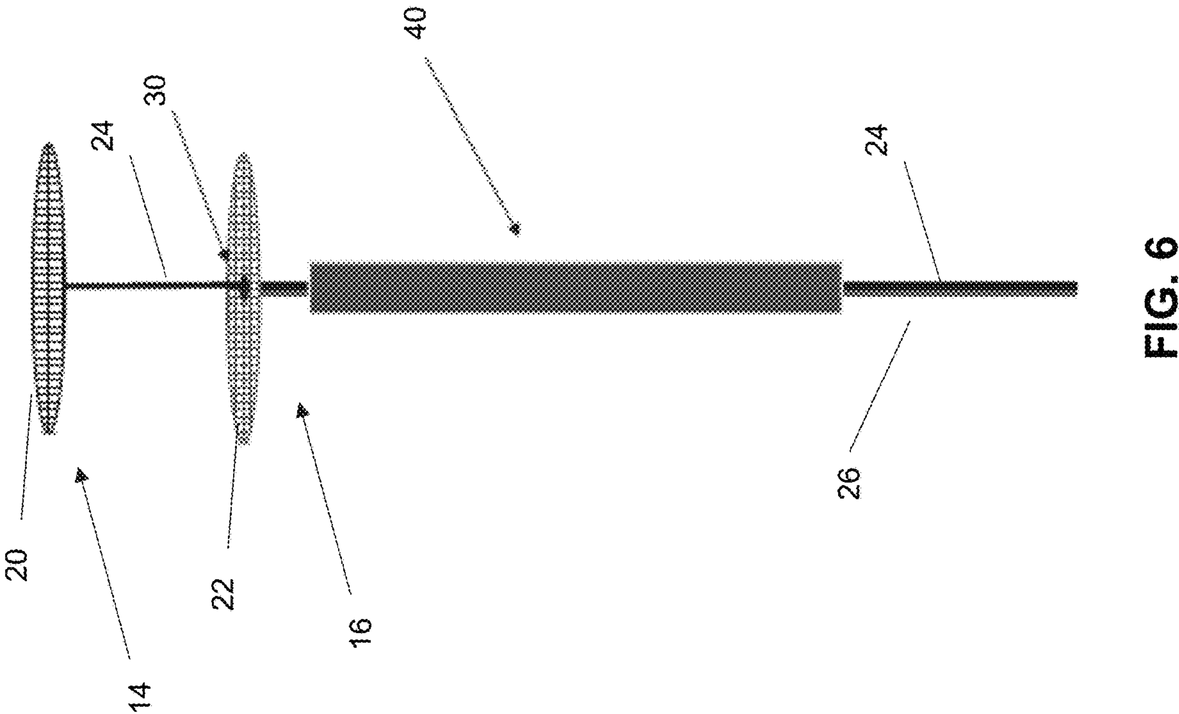
Figure 7:
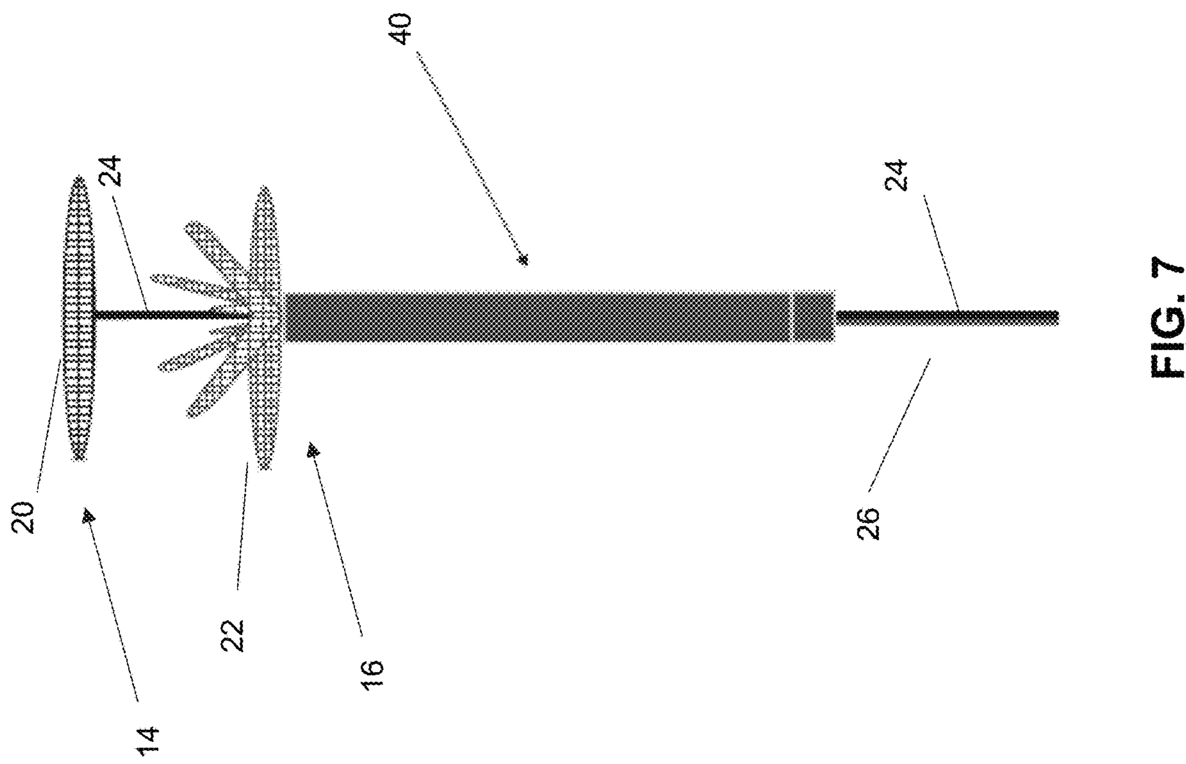
Figure 8:
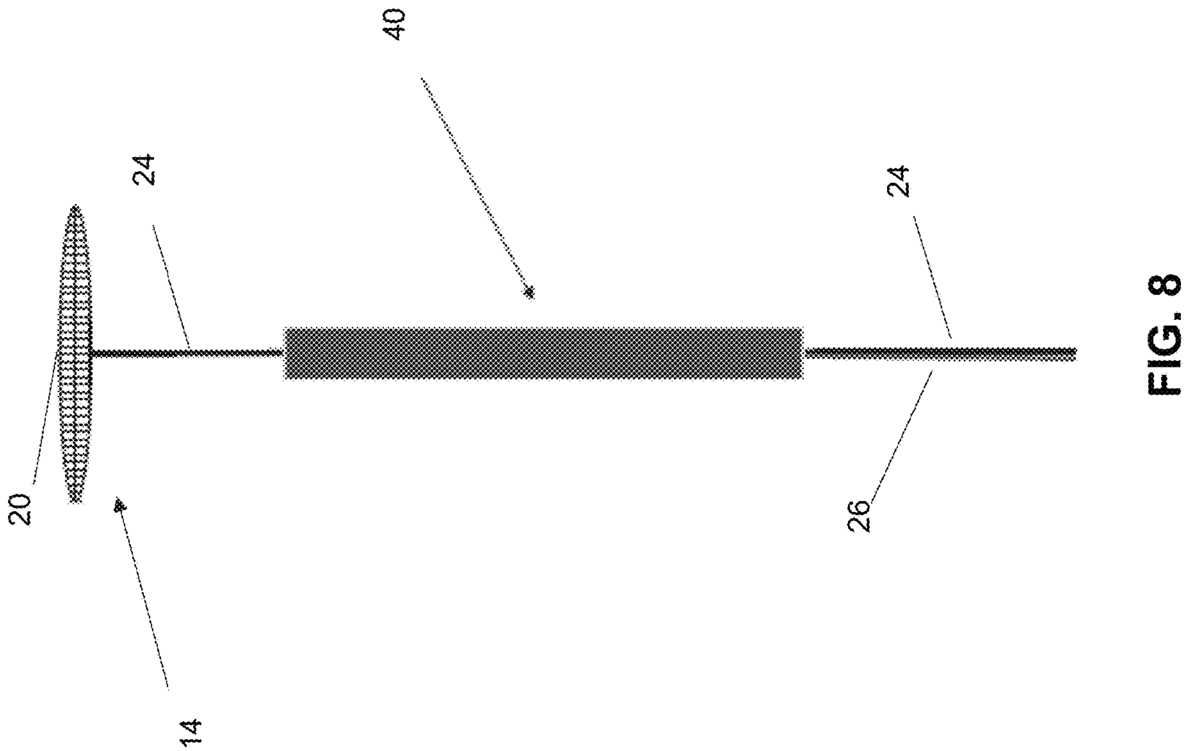
Figure 9:
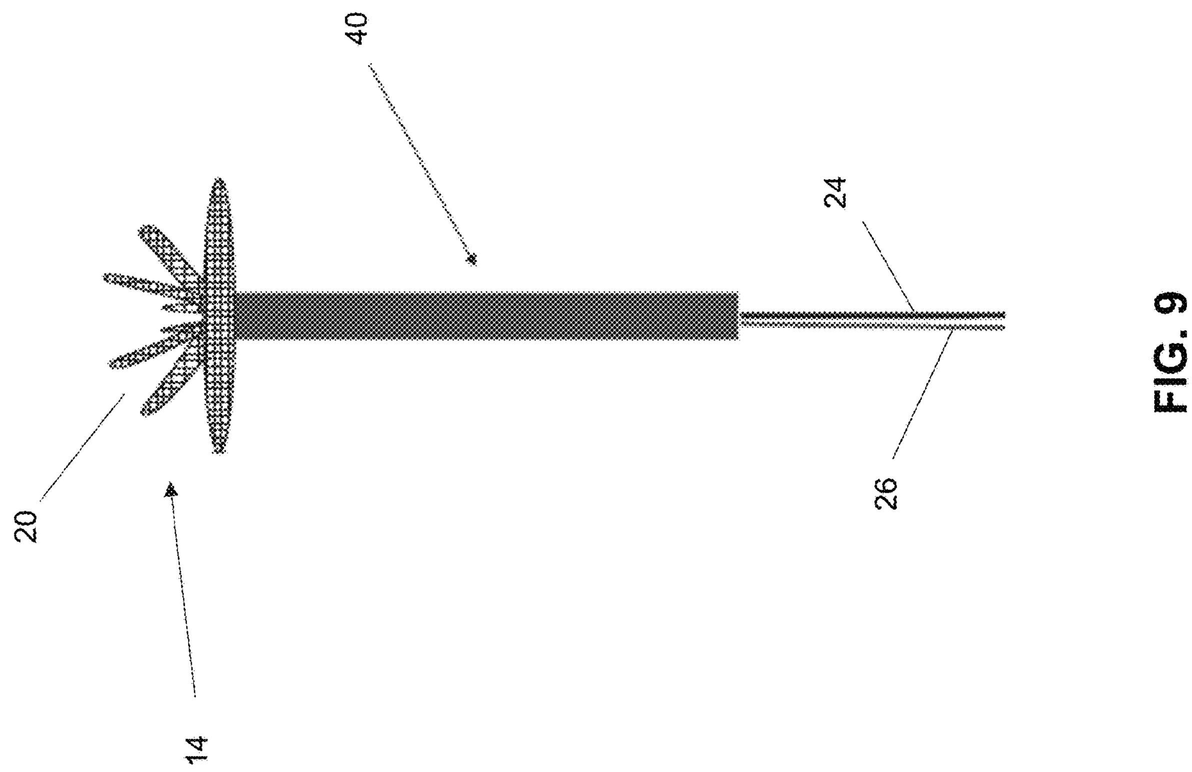

The ablation system 10 is loaded into the loader 40. As illustrated in FIG. 5, the RA RF applicator 16 and its cable 26 are loaded into loader 40. The LA RF applicator 14 is then loaded into loader 40 with its cable 24 threaded through the central hole 30 of the disc 22 of the RA RF applicator 16 (FIG. 6). The RA RF applicator 16 is retracted and collapsed into the loader 40 (FIGS. 7-8). As shown in FIG. 7, the disc 22 is shown collapsing into loader 40. LA RF applicator 14 is subsequently collapsed into the loader 40 (FIG. 9). The loader 40 is then fit onto the back end of the transseptal sheath 12, and the ablation system is advanced through the sheath 12 to the heart.

Figure 10:
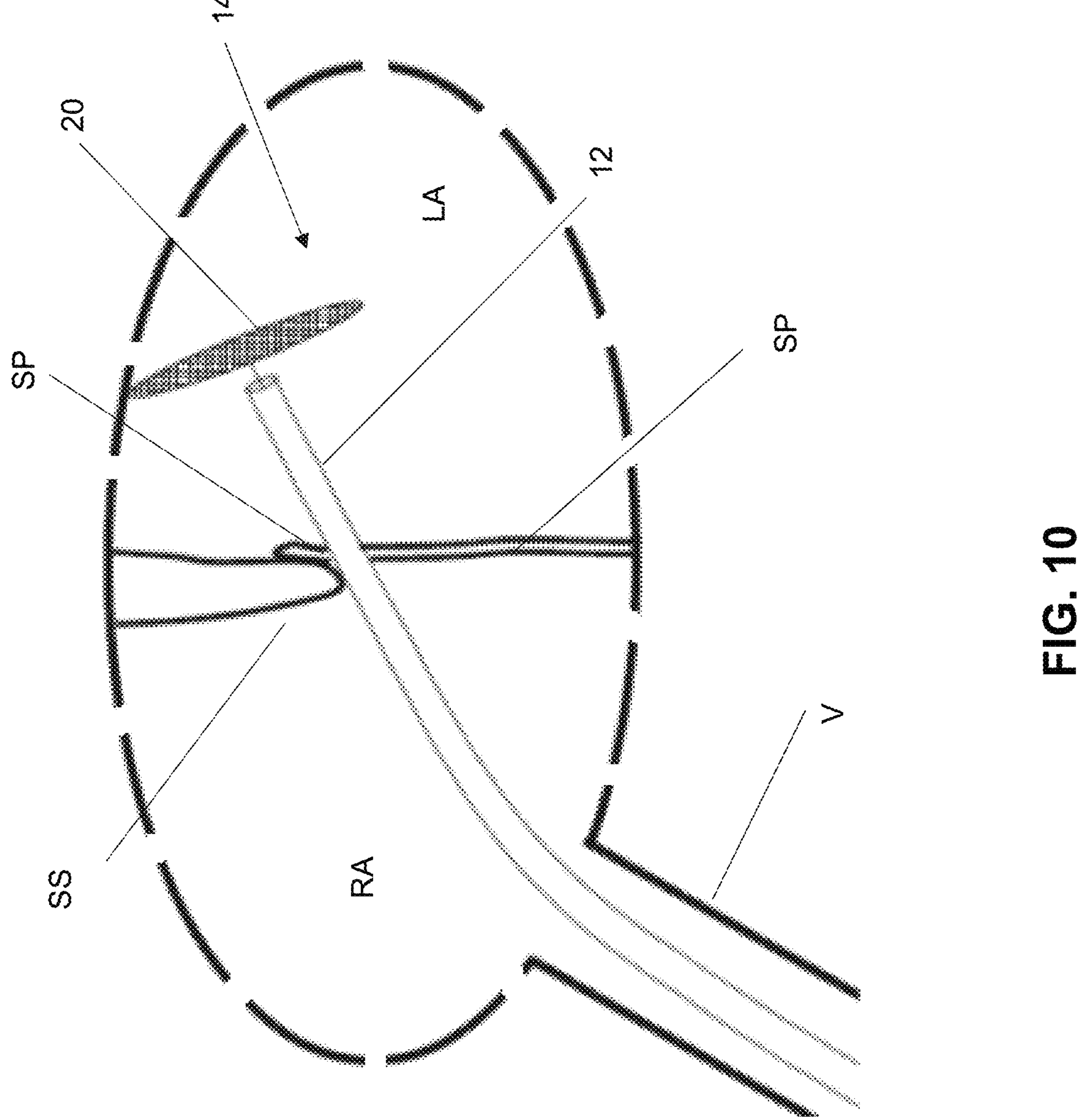
FIGS. 10-12 illustrate several stages of inserting a first disc in accordance with an exemplary embodiment of the disclosed subject matter.
Figure 11:
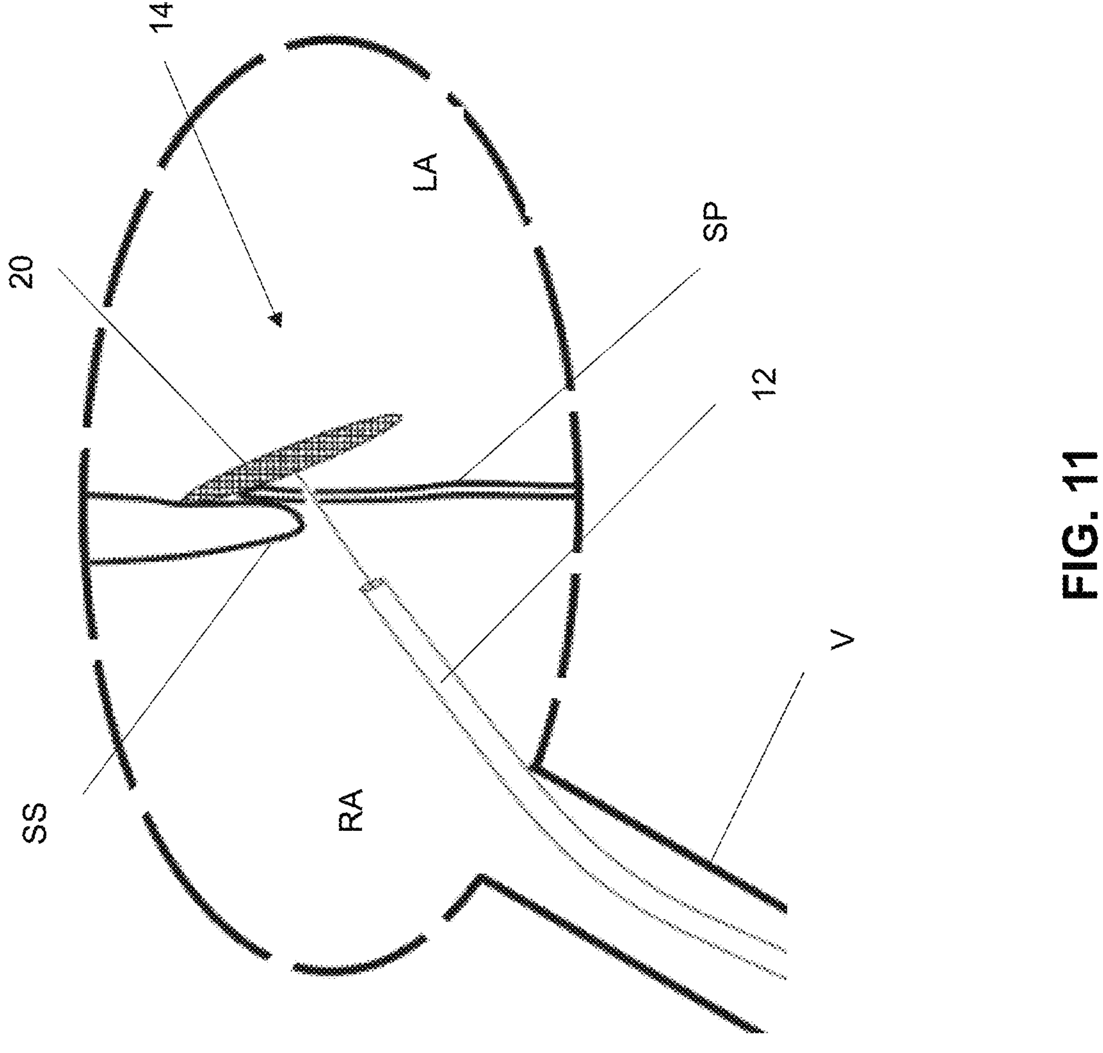
Figure 12:
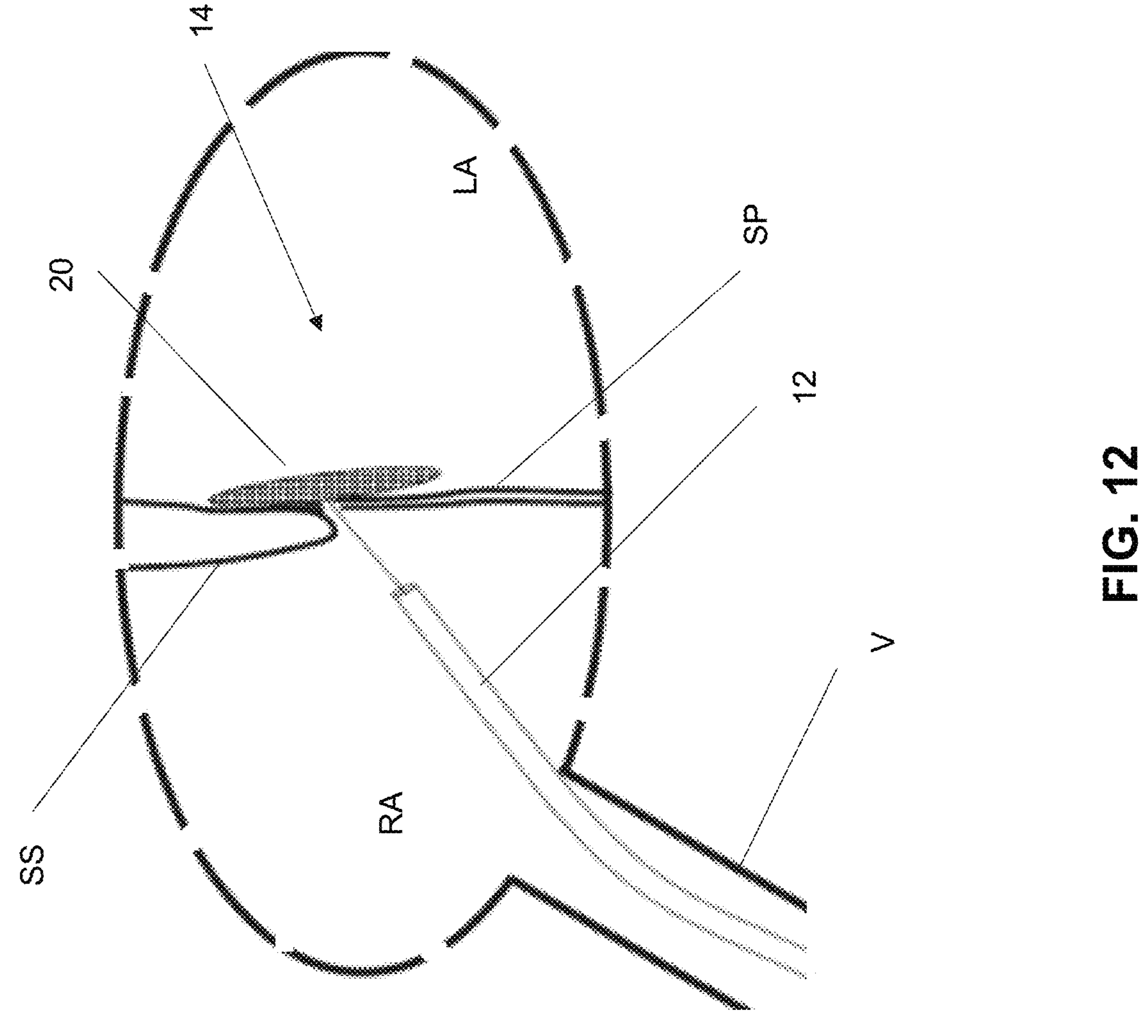

With transseptal sheath 12 in position through the PFO (FIG. 2) or alternatively through a transseptal puncture SP (FIG. 3), the LA RF applicator 14 is advanced into the LA, and the disc 20 is allowed to open to its expanded disc-shaped configuration (FIG. 10). The disc 20 is then pulled back towards the septum (FIG. 11), and into apposition to the LA side of the septum, pulling the septum primum against the septum secundum (FIG. 12). Subsequently or concurrently, the sheath 12 is then withdrawn into the RA.

Figure 13:
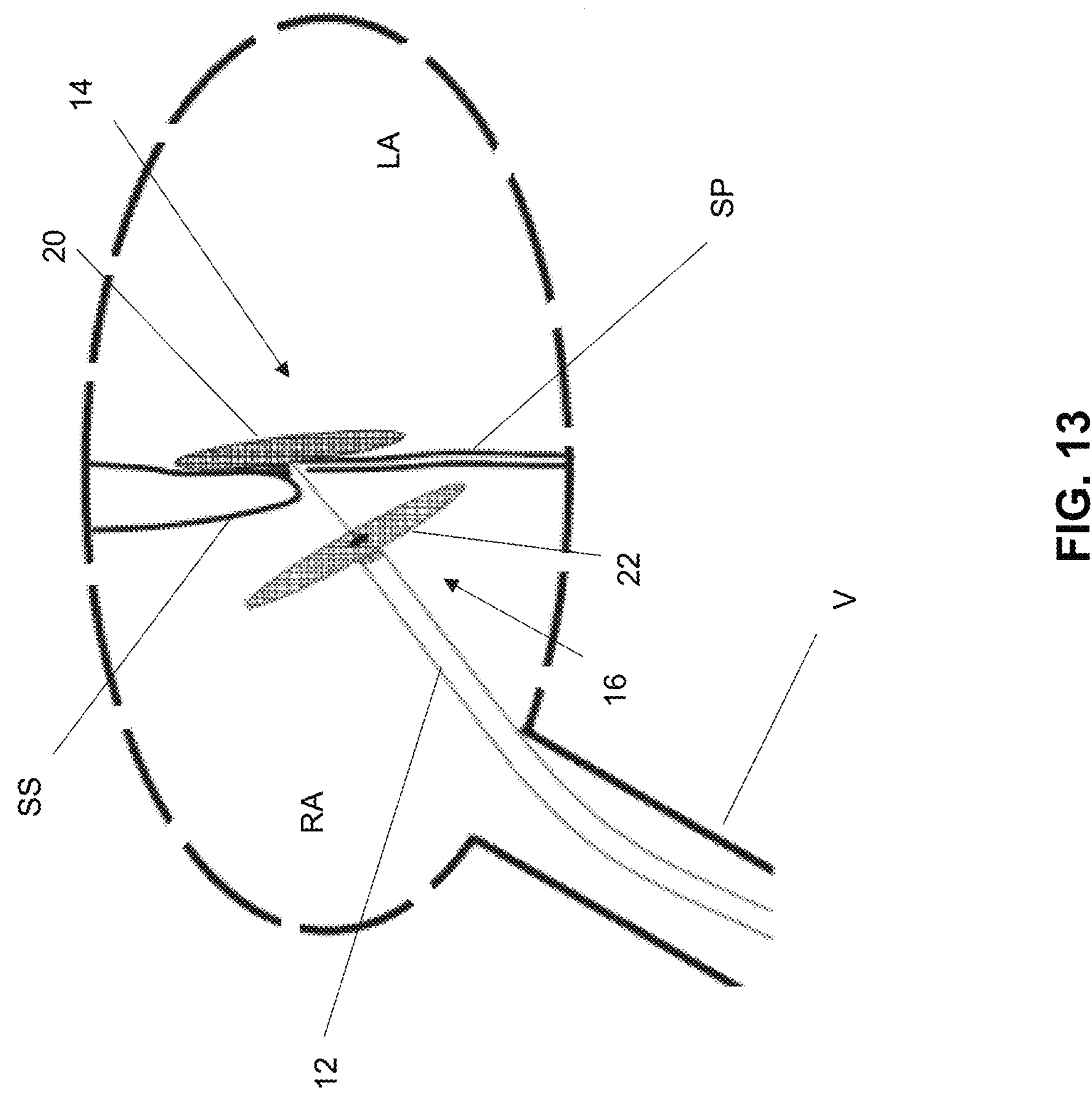
FIGS. 13-14 illustrate several stages of inserting a second disc in accordance with an exemplary embodiment of the disclosed subject matter.
Figure 14:
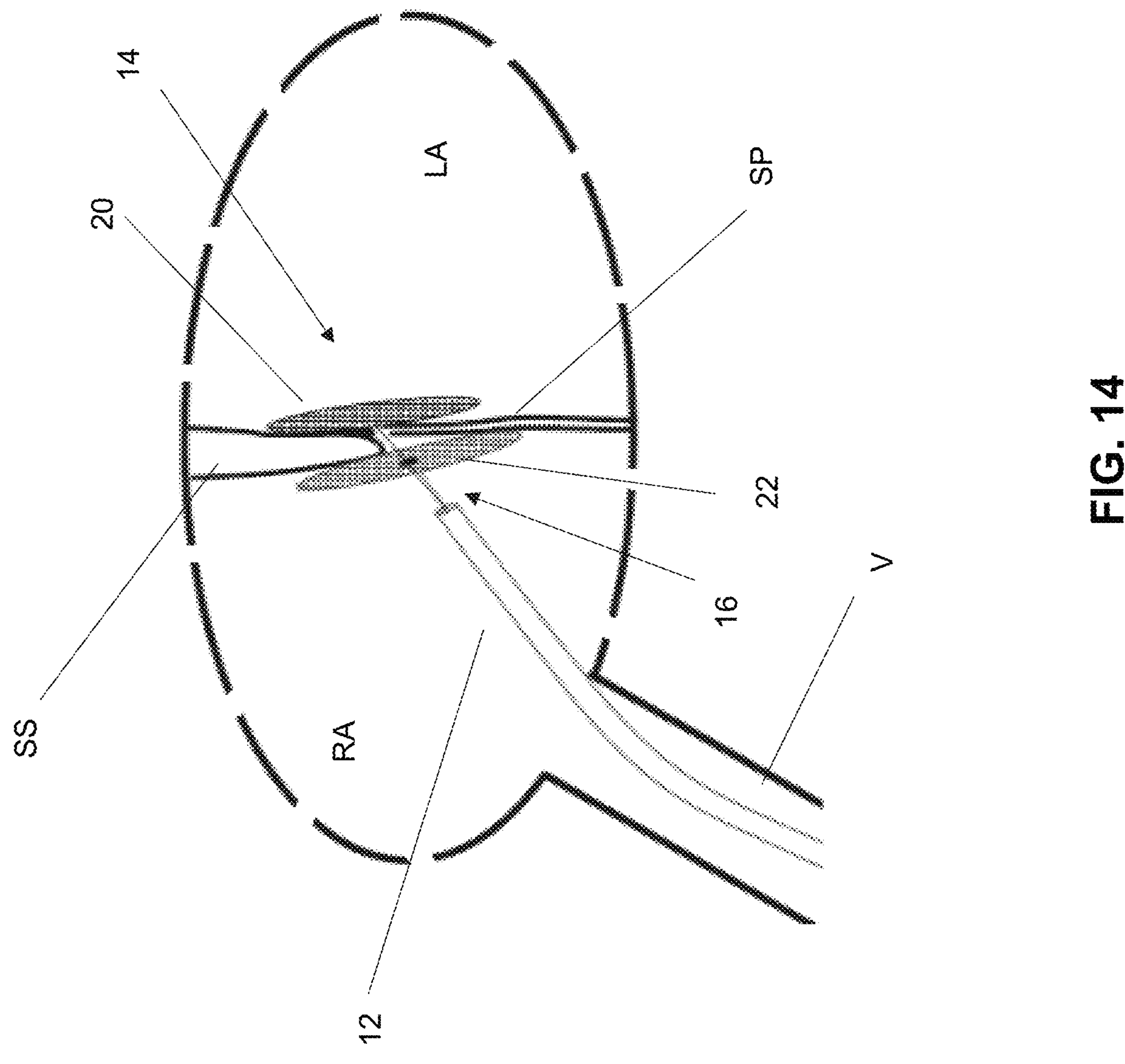

The RA RF applicator 16 is then advanced and disc 22 is allowed to open to its expanded disc-shaped configuration in the RA (FIG. 13), and because of the coaxial design of the two discs, is advanced towards the septum. The two discs 20/22 align directly opposite one another. The discs 20/22 are drawn together tightly (pulling the LA RF applicator 14 and advancing the RA RF applicator 16) to pull the septal flap shut (FIG. 14), thereby apposing the tissues of septum primum and septum secundum. The cables are then clamped in position (Co-pilot type arrangement).

Figure 15:
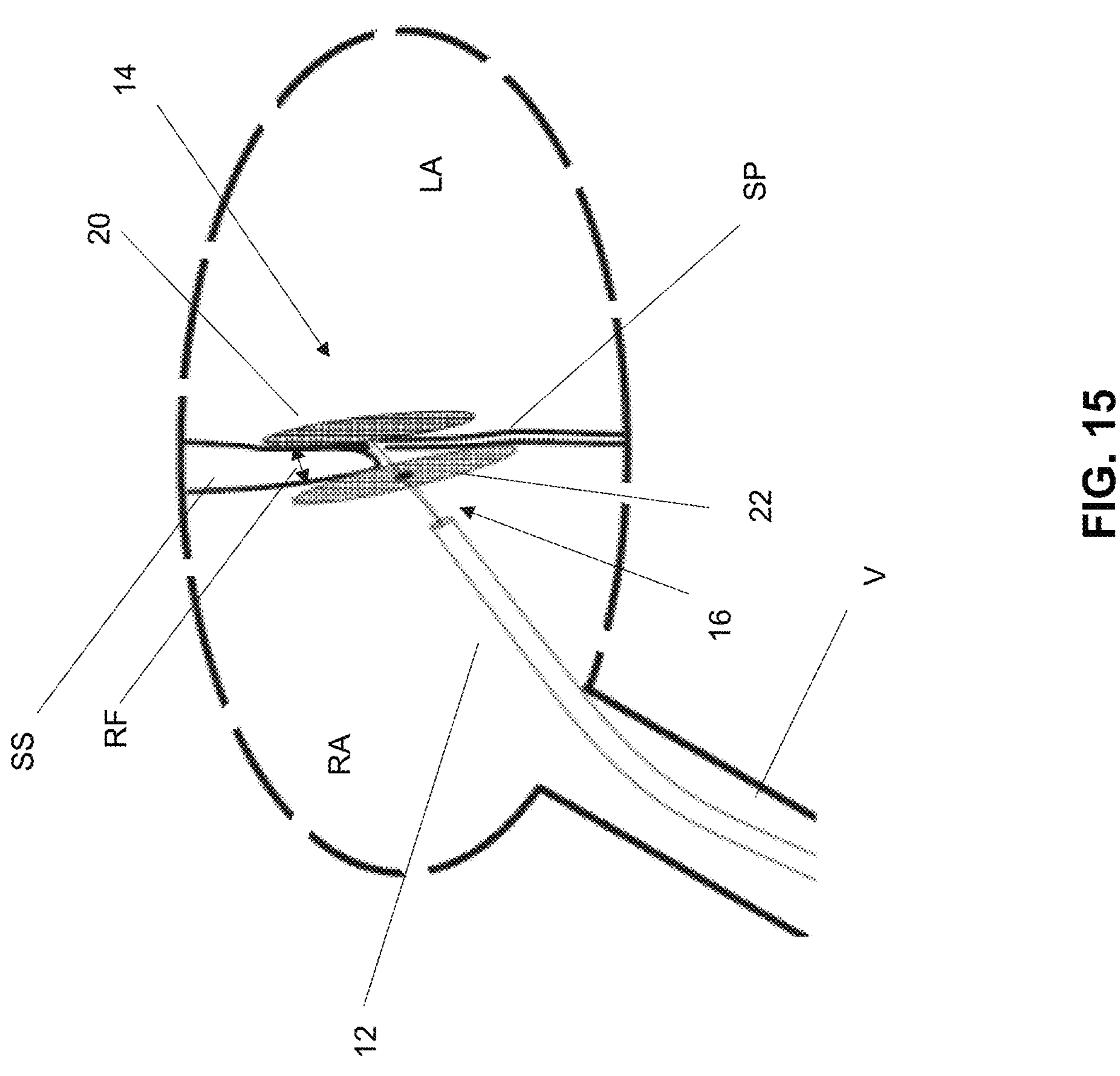
FIG. 15 illustrates a stage applying RF energy to the first and second disc in accordance with an exemplary embodiment of the disclosed subject matter.

The electrically isolated cables 24/26, attached to the two discs 20/22 are then connected to the RF source, one to the energy source pole and one to the ground pole. Bipolar RF energy is applied from one disc to the other to anneal the tissues (stylistically represented by arrow RF between discs 20-22) (FIG. 15). Optimal intensity and duration of energy application will depend on the specific anatomy of each individual septum, and may vary from patient to patient. This energy application is less than that used to perform transseptal puncture (vaporizing the tissue), is distributed over a larger surface from disc to disc, and can be applied for a longer duration of time, as needed.

Figure 16:
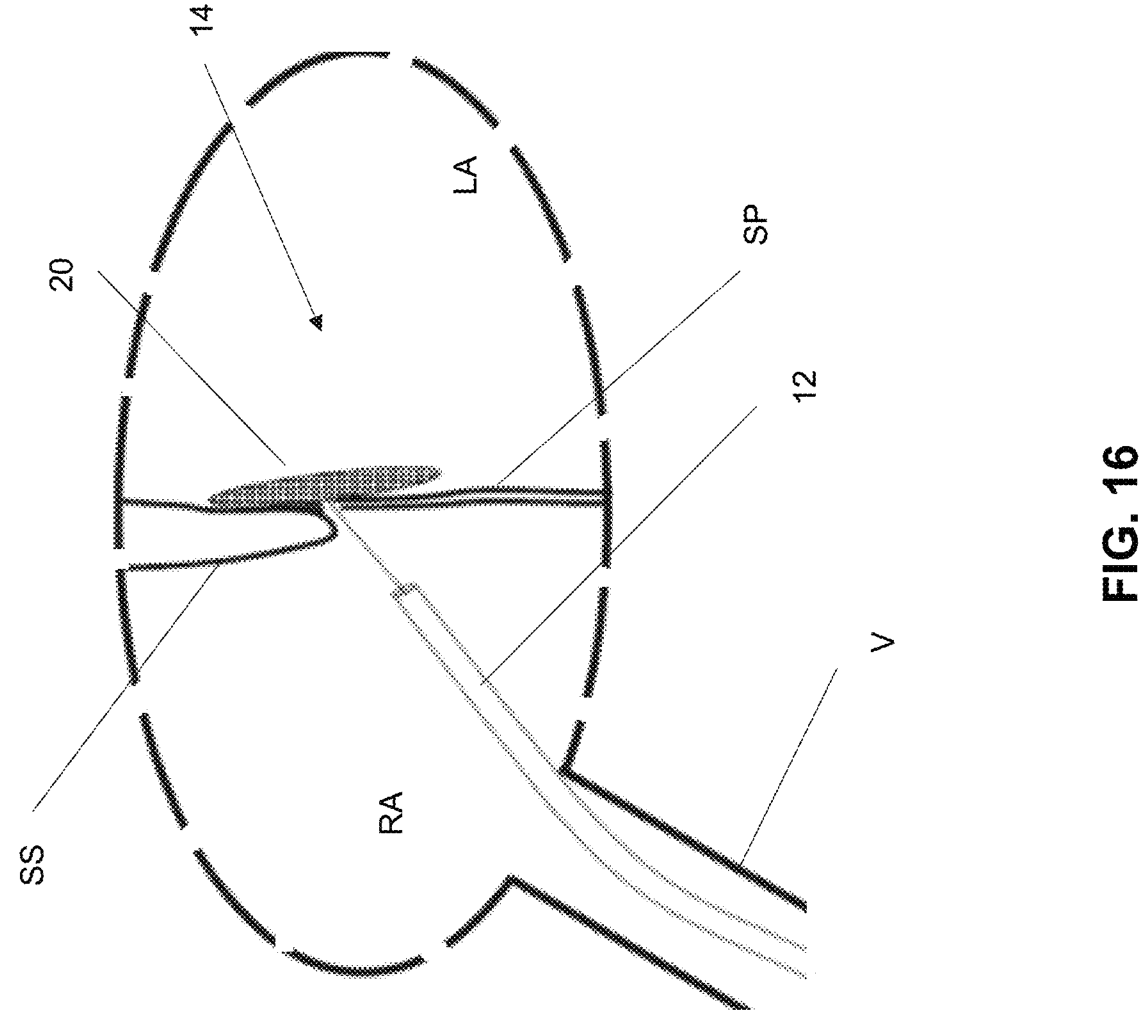
FIGS. 16-17 illustrate several stages of removing the first and second discs in accordance with an exemplary embodiment of the disclosed subject matter.
Figure 17:
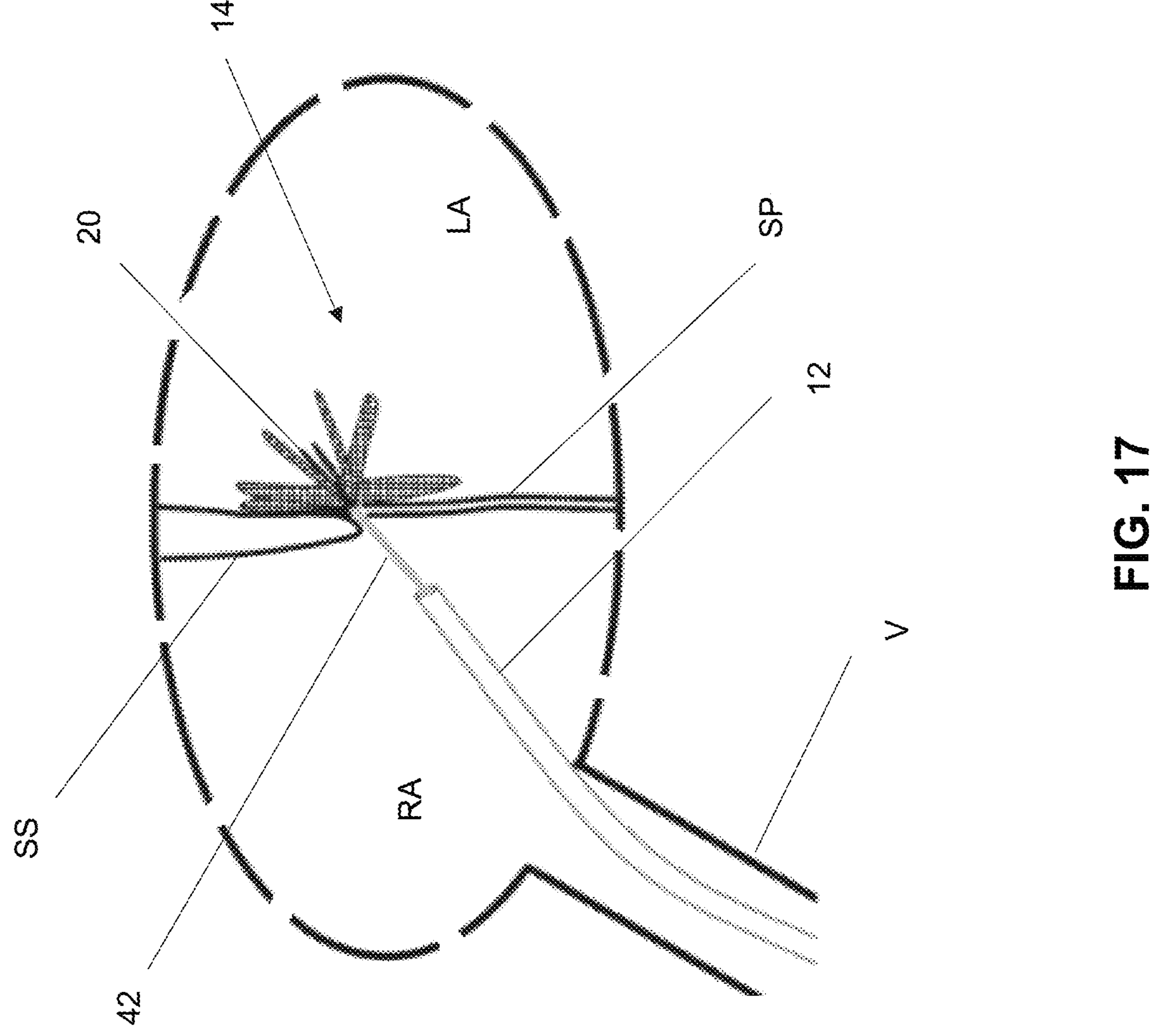

Once the RF energy application is completed, follow-up echo assessment can be done (e.g., by echo imaging with agitated saline injection). If the closure result is incomplete, additional energy application may be applied. If acceptable, the two cables are detached from the RF source, the cables unclamped, and the disc 22 of the RA RF applicator 16 is collapsed back into the transseptal sheath 12 and removed from the body (FIG. 16). A thin rigid tubule 42 is advanced over the LA RF applicator cable 24, through the transseptal sheath 12 and through the septum. The LA RF applicator is advanced off the septum into the LA, and disc 20 is collapsed into the tubule 42 and withdrawn from the body (FIG. 17). Follow-up echo assessment can be performed. If closure is incomplete, the procedure can be repeated.

Sheaths are removed, and hemostasis is obtained at the groin as per routine cath-lab procedures. The patient is observed as per the usual practice of the physician and can be discharged home later the same day.

Alternate strategy could include subsequent application of energy at the RA side of the septum to seal the small residual defect from the LA RF applicator tubule sheath, but is likely not necessary to achieve a subsequent complete seal.

It is understood that the subject matter described herein is not limited to particular embodiments described, as such may, of course, vary. Accordingly, nothing contained herein should be understood as limiting the scope of the disclosure. It is also understood that the terminology used herein is for the purpose of describing particular embodiments only, and is not intended to be limiting. Where a range of values is provided, it is understood that each intervening value between the upper and lower limit of that range and any other stated or intervening value in that stated range, is encompassed within the disclosed subject matter.

What is claimed is:

1. A system for transseptal closure of the patent foramen ovale (PFO) comprising:

a tubular loader defining a lumen;

a first RF applicator comprising a first cable defining a distal end and a proximal end;

a first disc coupled to the distal end of the first cable and insertable into the left atrium, the first disc fabricated from an electrically conductive, resilient material that achieves an expanded disc-shaped configuration when deployed from the tubular loader and a collapsed configuration when positioned within the lumen of the tubular loader; and a first contact at the proximal end of the first cable for electrical attachment to a bipolar RF generator;

a second RF applicator comprising a second cable defining a distal end and a proximal end;

a second disc coupled to the distal end of the second cable and insertable into the right atrium, the second disc fabricated from an electrically conductive, resilient material that achieves an expanded disc-shaped configuration when deployed from the tubular loader and a collapsed configuration when positioned within the lumen of the tubular loader; and a second contact at the proximal end of the second cable for electrical attachment to the bipolar RF generator, the first disc being located distal to the second disc, the first disc and the second disc being deployable directly from the lumen of the tubular loader, when in the collapsed configuration, the first disc contacting the lumen of the tubular loader and when in the collapsed configuration, the second disc contacting the lumen of the tubular loader, and the system configured for withdrawal of the first disc and the second disc into the lumen following deployment of the first disc and the second disc.

2. The system of claim 1, wherein the first and second discs are configured to expand to the expanded disc-shaped configuration upon deployment from the lumen of the tubular loader.

3. The system of claim 1, further comprising a tubular withdrawal member defining a lumen and insertable over the first cable and the first disc to collapse the first disc into the lumen of the tubular withdrawal member for withdrawal from the left atrium across the septum.

4. The system of claim 1, wherein the diameter of the first and second discs is about 1.5 cm to about 3.5 cm.

5. The system of claim 1, wherein the second disc defines an aperture for the first cable to extend therethrough.

6. The system of claim 1, wherein the first and second discs are fabricated from a shape memory alloy.

7. The system of claim 6, wherein the first and second discs are fabricated from nitinol.

8. The system of claim 1, wherein the length of the first and second cables is about 80 cm.

9. The system of claim 1, further comprising a transseptal sheath.

10. A method of transseptal closure of the patent foramen ovale (PFO) comprising:

inserting a distal end of a tubular loader into the left atrium of a subject's heart via the right atrium and the septum;

deploying a first RF applicator directly from the tubular loader across the septum and into the left atrium, the first RF applicator comprising a first cable and a first disc fabricated from an electrically conductive, resilient material in a collapsed configuration within and contacting the tubular loader;

deploying the first disc beyond the distal end of the tubular loading such that the first disc is allowed to resiliently expand from the collapsed configuration to an expandable disc-shaped configuration;

withdrawing the first RF applicator such that the first disc is in apposition against the septum;

withdrawing the tubular loader such that the distal end of the tubular loader is within the right atrium;

deploying a second RF applicator directly from the tubular loader beyond the distal end of the tubular loader and into the right atrium, the second RF applicator comprising a second cable and a second disc fabricated from an electrically conductive, resilient material such that the second disc is allowed to resiliently expand from a collapsed position contacting the tubular loader into an expanded disc-shaped configuration;

advancing the second RF applicator such that the second disc is in apposition against the septum, thereby approximating the septum primum and septum secundum; and applying bipolar RF energy across the first and second disc to the septum via the first and second cables.

11. The method of claim 10, wherein inserting the distal end of the tubular loader into the left atrium of a subject's heart via the right atrium and the septum comprises inserting the tubular loader through the PFO.

12. The method of claim 10, wherein inserting the distal end of the tubular loader into the left atrium of a subject's heart via the right atrium and the septum comprises inserting the tubular loader through a transseptal puncture.

13. The method of claim 10, wherein deploying the first RF applicator and deploying the second RF applicator comprise providing the first and second discs having a diameter of about 1.5 cm to about 3.5 cm.

14. The method of claim 10, wherein deploying the second RF applicator comprises providing an aperture in the second disc for the first cable to extend therethrough.

15. The method of claim 10, wherein deploying the first RF applicator and deploying the second RF applicator comprises providing the first and second discs fabricated from a shape memory alloy.

16. The method of claim 10, further comprising, after applying bipolar RF energy across the first and second disc to the septum, withdrawing the second disc into the lumen of the tubular loader.

17. The method of claim 16, further comprising, providing a tubular withdrawal member.

18. The method of claim 17, further comprising advancing the tubular withdrawal member over the second cable into the right atrium.

19. The method of claim 18, further comprising withdrawing the first disc into the lumen of tubular withdrawal member.

20. The method of claim 19, further comprising withdrawing the tubular withdrawal member and the second RF applicator from the subject's heart.

* * * * *